(12) United States Patent
Nordin

(10) Patent No.: US 6,402,519 B1
(45) Date of Patent: Jun. 11, 2002

(54) ANCHORAGE ELEMENTS AND AUXILIARY INSTRUMENTS FOR DENTISTRY

(75) Inventor: Harald E. Nordin, Brent (CH)

(73) Assignee: Harald Nordin SA (CH)

( * ) Notice: Subject to any disclaimer, the term of this patent is extended or adjusted under 35 U.S.C. 154(b) by 0 days.

(21) Appl. No.: 09/650,030

(22) Filed: Aug. 28, 2000

(30) Foreign Application Priority Data

Aug. 27, 1999 (EP) .............................. 99810776

(51) Int. Cl.[7] .................................. A61C 5/08
(52) U.S. Cl. ..................................... 433/220
(58) Field of Search .............................. 433/220, 221, 433/224, 225, 226

(56) References Cited

U.S. PATENT DOCUMENTS

| | | | |
|---|---|---|---|
| 4,334,865 A | | 6/1982 | Borle ........................ 433/221 |
| 4,443,507 A | * | 4/1984 | Yamada et al. ............ 428/114 |
| 4,525,147 A | * | 6/1985 | Pitz et al. .................. 433/224 |
| 5,282,747 A | * | 2/1994 | Nordin ...................... 433/221 |
| 5,328,372 A | * | 7/1994 | Reynaud et al. ........... 433/220 |
| 5,564,929 A | * | 10/1996 | Alpert ....................... 433/224 |
| 5,603,616 A | * | 2/1997 | Fernandes .................. 433/175 |
| 5,816,816 A | | 10/1998 | Scharf ....................... 433/220 |

FOREIGN PATENT DOCUMENTS

| | | |
|---|---|---|
| DE | 3825601 | 3/1989 |
| EP | 0522221 | 1/1993 |
| FR | 2468353 | 5/1981 |
| FR | 2588181 | 4/1987 |
| FR | 2626167 | 7/1989 |
| GB | 2214087 | 8/1989 |

* cited by examiner

*Primary Examiner*—John J. Wilson
*Assistant Examiner*—Melba Bumgarner
(74) *Attorney, Agent, or Firm*—Ostrolenk, Faber, Gerb & Soffen, LLP

(57) ABSTRACT

The anchorage element for a tooth suprastructure, e.g. a root canal anchor, consists of a fiber-reinforced synthetic material in which the biaxially or multiaxially extending fibers are arranged in a braided netting. Such anchorage elements provide a high flexural and torsional strength, i.e. breaking resistance, as well as a high axial flexibility.

10 Claims, 1 Drawing Sheet

ANCHORAGE ELEMENTS AND AUXILIARY INSTRUMENTS FOR DENTISTRY

FIELD OF THE INVENTION

The present invention refers to an anchorage element, such as a root pin or a root canal anchor, consisting of a fiber-reinforced synthetic material in which the fibers extend biaxially or multiaxially, as well as to an auxiliary instrument used in the insertion of the anchorage element.

BACKGROUND OF THE INVENTION

Root pins resp. root canal anchors are known from the French Publication No. 2,588,181. This French publication discloses a number of pins which may consist of fiber-reinforced synthetic materials, as well as different manufacturing methods and different possible ways of arranging the fibers and embedding them in the synthetic materials.

The German Publication No. 38,25,601 discloses further root canal anchors consisting of fiber-reinforced synthetic materials where the fibers in the anchorage portion extend along the pin axis essentially while those in the retention head extend in a different direction, however in parallel to each other in each case.

SUMMARY OF THE INVENTION

It has been found, and tests have confirmed that the properties which are important in a root canal anchor, i.e. its torsional and flexural resistance, and thus also its breaking resistance, are insufficient in the anchors of the prior art, and it is therefore an object of the present invention to provide an anchorage element having an increased flexural and torsional strength and thus an increased breaking resistance. This object is attained by an anchorage element wherein its fibers are arranged in the manner of a braided netting. Preferred embodiments of the invention are defined in the dependent claims.

DETAILED DESCRIPTION OF THE INVENTION

Figure 3:
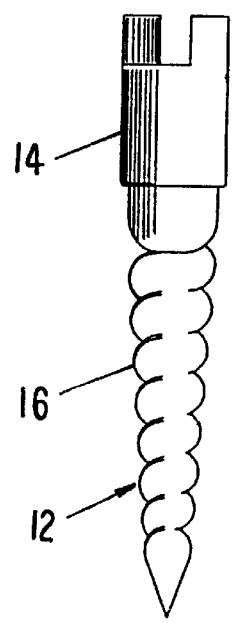
FIG. 3 shows another embodiment of an anchorage element including the invention.
Figure 4:
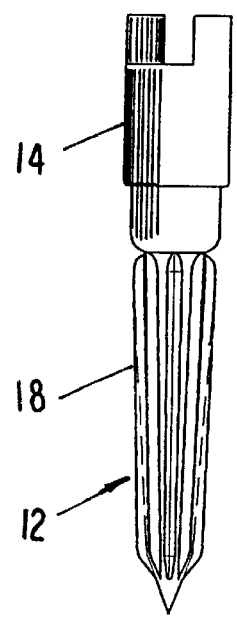
FIG. 4 shows an alternate embodiment of an anchorage element including the invention.

The invention will be explained in more detail in the following description. Since it appears that good torsional and flexural properties are independent from the shape and dimension of an anchorage element, the description refers to an anchorage element 10 such as a root canal anchor or a root pin in general. In a known manner, e.g. according to the cited references or to European Patent Application No. 522,221, it is composed of an anchorage portion 12 and of a head 14, the anchorage portion comprising a screw thread 16 in FIG. 3 or fins 18 in FIG. 4 or the like, depending on the anchorage type, while the head 14 may be in the form of an adhesion head, a retention head, or a flat head, known per se, designed to accept the suprastructure.

The known trimmers, enlargers and the like are made of metal, and their shapes are approximated to that of the anchored pins, naturally. In this context, it appears that the treatment is improved if the working surfaces of the auxiliary instruments have the same shape as the anchorage portions, thus allowing a perfect fastening of the pins, generally by means of a suitable cement.

Figure 1:
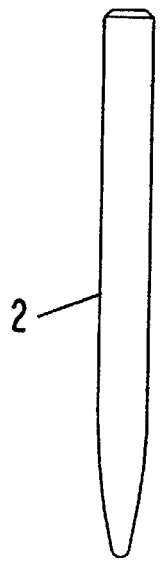
FIG. 1 is a side view of an anchorage element.
Figure 2:
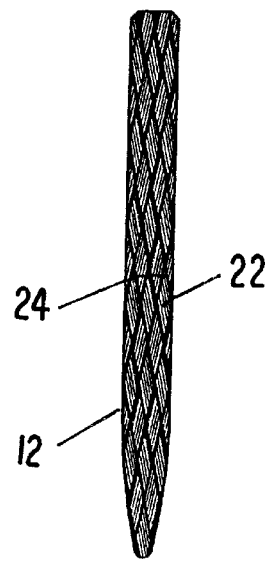
FIG. 2 is a side view of the anchorage portion of an anchorage element including the invention.

In the anchorage elements of the prior art, the fibers, i.e. carbon fibers or glass fibers, generally extend in the longitudinal axis of the pins. In order to increase the resistance to flexural and torsional forces as well as the axial flexibility, which results in a substantially increased breaking resistance, the fibers are no longer arranged axially but biaxially or multiaxially as seen at 22 in FIG. 2. According to the invention, the fibers are preferably braided. In the case of carbon fibers, four to twelve strands of 9,000 to 3,000 fibers each, and preferably six strands of 6,000 fibers each or 12 strands of 3,000 fibers each are used, for example, both resulting in the same carbon fiber content of approx. 65%. Preferred carbon fibers are high-strength fibers known under the designation HT or HTA.

As an embedding mass 24, an epoxy resin may e.g. be used. It is advantageous to use epoxy resins which are capable of a chemical bond with the cement and/or the material of the tooth suprastructure.

The invention is not limited to this particular kind of carbon fibers, but other suitable fibers of high strength can also be used, and the number of strands, resp. of fibers per strand may vary. In order to obtain a high breaking resistance, besides the arrangement of the fibers in the manner of a braided netting, it is important to ensure a high fiber content of 60 to 70%.

Instead of carbon fibers, it is also possible to use glass or quartz fibers. Furthermore, the invention is not limited to the use of epoxy resins, but other known synthetic embedding materials are also possible. The precise form of the braided netting is less important than the fact that it is a biaxial or multiaxial netting which ensures not only a high breaking resistance but also the axial flexibility necessary in order to absorb detrimental stresses or deformations appearing in the tooth and in the tooth suprastructure during chewing movements.

The use of trimmers, pre-trimmers, enlargers or similar auxiliary instruments having the same dimensions and shapes as the root canal anchors or root pins allows a high degree of conformity between the bore and the inserted pin, thereby ensuring a perfect anchorage. As already mentioned in the introduction, all known embodiments of root canal anchors and root pins may be manufactured from the fiber-reinforced synthetic material described above, and in addition to the known advantages in using non-metallic pins, the novel pins and root canal anchors offer a higher breaking resistance and a greater elasticity and thus an extended lifetime.

What is claimed is:

1. An anchor element for a tooth suprastructure, the anchor element comprising:
   an anchor pin made from a mass of synthetic material; and
   fibers embedded in said synthetic material for reinforcing said anchor pin to provide torsional and flexural strength, said fibers being arranged biaxially or multiaxially in the form of a braided netting and being carbon fibers which are braided in 4 to 12 strands of 9,000 to 3,000 fibers each.

2. The anchor element of claim 1, wherein said carbon fibers are high-strength carbon fibers.

3. The anchor element of claim 1, wherein said synthetic material is an epoxy resin.

4. The anchor element of claim 3, wherein said carbon fibers constitute 60% to 70% of the content of the anchor element.

5. The anchor element of claim 3, wherein said epoxy resin is selected so as to be able to establish a chemical bond with a dental cement and/or the tooth suprastructure.

6. The anchor element of claim 1, wherein said anchor pin comprises an anchoring portion and a head portion.

7. The anchor element of claim 6, wherein said anchoring portion includes a screw thread.

8. The anchor element of claim 6, wherein said anchoring portion includes fins.

9. An anchor element for a tooth suprastructure, the anchor element comprising:

an anchor pin made of a mass of synthetic material; and a braided netting embedded in said synthetic material and made of fibers for reinforcing said anchor pin to provide torsional and flexural strength, said fibers being arranged biaxially or multiaxially;

wherein said anchor pin comprises an anchoring portion and a head portion; and wherein said anchoring portion includes a screw thread.

10. An anchor element for a tooth suprastructure, the anchor element comprising:

an anchor pin made of a mass of synthetic material; and a braided netting embedded in said synthetic material and made of fibers for reinforcing said anchor pin to provide torsional and flexural strength, said fibers being arranged biaxially or multiaxially;

wherein said anchor pin comprises an anchoring portion and a head portion; and wherein said anchoring portion includes fins.

* * * * *